United States Patent [19]
Ariyan et al.

[11] 3,983,244
[45] Sept. 28, 1976

[54] METHOD OF CONTROLLING PESTS USING CERTAIN KETONES OF FURAN

[75] Inventors: Zaven Stephen Ariyan, Woodbury; Robert Edward Grahame, Jr., Waterbury; Winchester Loomis Hubbard, Woodbridge, all of Conn.

[73] Assignee: Uniroyal Inc., New York, N.Y.

[22] Filed: May 9, 1975

[21] Appl. No.: 575,910

Related U.S. Application Data

[62] Division of Ser. No. 306,044, Nov. 13, 1972, Pat. No. 3,904,760.

[52] U.S. Cl. ............................... 424/275; 424/45; 424/285; 424/357
[51] Int. Cl.² ...................... A01N 9/00; A01N 9/12
[58] Field of Search ........................... 424/285, 275

[56] References Cited
UNITED STATES PATENTS
3,723,477   3/1973   Pelosi, Jr. ..................... 424/285 X OTHER PUBLICATIONS
Journal of Economic Entomology, 6/1963, vol. 56, No. 3., pp. 261 to 265.

*Primary Examiner*—Dale R. Ore
*Attorney, Agent, or Firm*—James J. Long

[57] ABSTRACT

Certain ketones of substituted furans and thiophenes of the formula

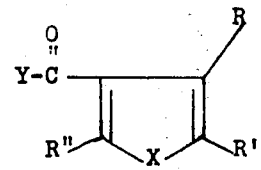

where Y is for example 3-(2,5-dichlorothienyl), o-bromophenyl, etc., the R's are for example hydrogen, halogen, etc., and X is oxygen or sulfur, are useful for controlling pests, particularly acarids (mites and ticks), insects and nematodes.

14 Claims, No Drawings

METHOD OF CONTROLLING PESTS USING CERTAIN KETONES OF FURAN

This is a division of application Ser. No. 306,044 filed Nov. 13, 1972, now U.S. Pat. No. 3,904,760.

This invention relates to a method of controlling pests, including acarids, using certain ketones of substituted furans and thiophenes.

British Pat. No. 1,228,744, Boots Pure Drug Co., issued Apr. 15, 1971, discloses control of nematodes with certain ketones of substituted furans or thiophenes, wherein the ketone group is in the 2-position of the furan or thiophene ring. In contrast, in the presently employed chemicals the ketone group is in the 3-position of the furan or thiophene ring; such chemicals have, surprisingly, been found to be effective acaricides.

U.S. Pat. No. 2,690,413, Janes et al., Sept. 24, 1954, discloses control of insects and nematodes by fumigation, using certain acetylated halogenated thiophenes and thiolanes. The chemicals used in the present invention are not acetylated bodies, and unexpectedly have acaricidal properties.

Y. L. Goldfarb & M. S. Kondakova., Izvest. Adad. Nauk. S.S.S.R., Otdel. Khim. Nauk. 1956, 495-504; CA: 1956: 16745c, disclose bis-3-(2,5-dimethyl-thienyl)-ketone.

Ng. Ph. Buu — Hoi and Denise Lavit, J. Chem. Soc. 1958, 1721-3 (C.A. 52, 16330 i) disclose 2,5-dichloro-3-(2-thenoyl) thiophene.

The chemicals employed as pesticides in the pest control method of the invention are ketones of furans and thiophenes having the formula

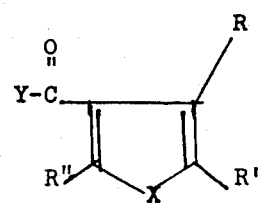

where Y represents a substituted or unsubstituted heterocyclic radical, a substituted or unsubstituted aromatic radical, or an alkenyl radical, R, R' and R'' are the same or different and may be hydrogen, alkyl or halogen, and X is oxygen or sulfur.

In the chemicals employed in the invention, preferred values for Y are $C_2-C_8$ alkenyl (e.g., vinyl, propenyl, butenyl, pentenyl, octenyl) or furyl, thienyl and phenyl without substitution or furyl, thienyl and phenyl substituted with one, two, or more substitutents (such as halogen [e.g., chlorine, bromine], lower alkyl [e.g., methyl, ethyl], and the like), R is preferably hydrogen, halogen (e.g., chlorine, bromine), or $C_1-C_8$ alkyl (e.g., methyl, ethyl, butyl, octyl) and R' and R'' are preferably halogen (e.g., chlorine, bromine) or $C_1-C_8$ alkyl (e.g., methyl, ethyl, butyl, octyl), X being of course oxygen or sulfur as previously indicated. Most preferred are chemicals in which Y is a heterocyclic or aromatic moiety.

The pesticidal chemicals useful in the invention are typically prepared by reacting, according to a Friedel-Crafts synthesis, a 2,5-disubstituted or 2,4,5-trisubstituted furan or thiophene with an appropriate acid chloride (source of the

group) in the presence of aluminum chloride according to the equation:

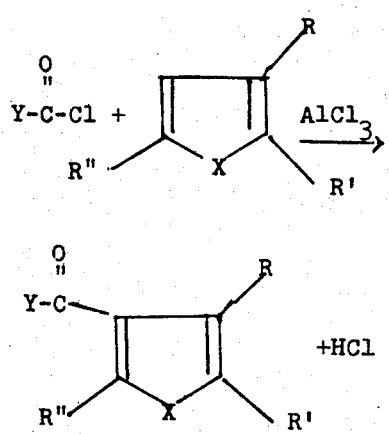

The acid chlorides employed may be alkenyl, aromatic or substituted aromatic, heterocyclic or substituted heterocyclic. Among the starting acid chlorides are those of the formula

where Y is an alkenyl group having 2 to 8 carbon atoms. Acid chlorides leading to new chemicals of the invention also include those of the formulas:

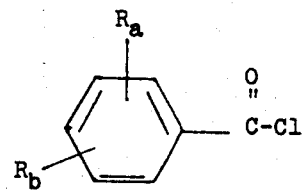

where $R_a$ and $R_b$ are the same or different and are hydrogen or substituents such as halogen, alkyl, etc.; also

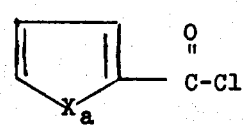

where $X_a$ is oxygen or sulfur, and

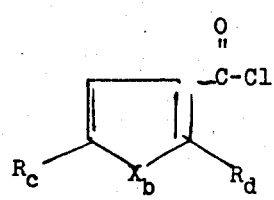

where $R_c$ and $R_d$ are the same or different and are hydrogen or various substituents such as halogen, alkyl, etc. and $X_b$ is oxygen or sulfur.

Preferred chemicals include those in which Y is 2-thienyl or 3-(2,5-dihalothienyl), X is sulfur, R is hydrogen, and R' and R'' are halogen.

Almost all of the present ketones are thick viscous oils somewhat yellow in color and they may be distilled readily at reduced pressures. They are soluble in most organic solvents. These thick oils may gradually solidify on standing over a period of time. They are usually prepared in 50–90% yield by the method described.

The principal pests against which the present biocidal process is employed are acarids such as mites and ticks, although the chemicals are also remarkable for their effectiveness in the control of other pests, notably insects and nematodes. Mites and insects are important in agriculture and as pests of man and animals. Nematodes are also important pests, both in agriculture and as internal parasites of man and animals. The chemicals of the present invention have the ability to destroy parasitic nematodes and their eggs and larvae.

Pest control may be accomplished by various methods including soil application for control of plant parasitic nematodes, foliar application for mite and insect control, and dissolving of the chemicals in water for the control of aquatic pests such as mosquito larvae.

The invention is applicable to control of such mites as apple rust mite *Aculus shlechtendali* (Nalepa) Banks grass mite *Oligonychus pratensis* (Banks), brown mite *Bryobia arborea* Morgan & Anderson, citrus red mite *Panonychus citri* (McGregor), citrus rust mite *Phyllocoptruta oleivora* (Ashmead), clover mite *Bryobia praetiosa* Koch, cyclamen mite *Steneotarsonemus pallidus* (Banks), European red mite *Panonychus ulmi* (Koch), McDaniel spider mite *Tetranychus mcdanieli* McGregor, Pacific spider mite *Tetranychus pacificus* McGregor, peach silver mite *Aculus cornutus* (Banks), six-spotted mite *Eotetranychus sexmaculatus* (Riley), straberry spider mite *Tetranychus atlanticus* McGregor, Texas citrus mite *Eutetranychus banksi* (McGregor), two-spotted spider mite *Tetranychus urticae* (Koch), and Willamette mite *Eotetranychus willamettei* McGregor, as well as such plant parasitic nematodes as root knot *Meloidogyne incognito*, sting *Belonolaimus longicaudatus*, surgarbeet *Heterodera schachtii*, lance *Hoplolaimus sp.*, stubby root *Trichodorus christiei*, awl *Dolichodorus heterocephalus*; also such saprophytic nematodes as *Panogrellus redivivus* such insects as the yellow fever mosquito *Aedes aegypti*.

In general, the present pesticidal agents may be applied in various manners. They may be applied to loci to be protected against pests as dusts when admixed with or absorbed in powdered solid carriers, such as various mineral silicates, e.g., mica, talc, pyrophillite and clays, or as liquids or sprays when in a liquid carrier, as in solution in a suitable solvent, such as acetone, toluene or kerosene, or dispersed in a suitable non-solvent medium, for example, water. In protecting plants (the term including plant parts), which are subject to attack by mites or other pests, the chemicals are preferably applied as aqueous emulsions containing a surface-active dispersing agent, which may be an anionic, non-ionic or cationic surface-active agent. Such surface-active agents are well known and reference is made to U.S. Pat. No. 2,547,724, columns 3 and 4 for detailed examples of the same. The chemicals may be mixed with such surface-active dispersing agents, with or without an organic solvent, as insecticidal concentrates for subsequent addition of water to make aqueous suspensions of the chemicals of the desired concentration. The chemicals may be admixed with powdered solid carriers, such as mineral silicates, together with a surface-active dispersing agent so that a wettable powder may be obtained, which may be applied directly to loci to be protected against pests, or which may be shaken up with water to form a suspension of the chemical (and powdered solid carrier) in water for application in that form. The chemicals may be applied to loci to be protected against pests by the aerosol method. Solutions for the aerosol treatment may be prepared by dissolving the chemical directly in the aerosol carrier which is liquid under pressure but which is a gas at ordinary temperature (e.g. 20°C.) and atmospheric pressure, or the aerosol solution may be prepared by first dissolving the chemical in a less volatile solvent and then admixing such solution with the highly volatile liquid aerosol carrier. The chemicals may be used admixed with carriers that are active of themselves, for example, other insecticides, fungicides, or bactericides.

The following preparations illustrate the synthesis of chemicals employed in the invention.

CHEMICAL 1

Preparation of 2-Thenoyl-3-(2,5-dibromothiophene)

To 48.2 gr. (0.2 mole) of 2,5-dibromothiophene and 29.2 gr. (0.2 mole) of 2-thenoyl chloride in 400 c.c. of dry carbon disulfide, anhydrous aluminum chloride (26.6 gr., 0.2 mole) is gradually added with efficient stirring at room temperature. A purple coloration gradually develops and HCl is evolved. This mixture is well stirred overnight and heated on a steam bath for two more hours prior to work up. The organic layer is then separated and washed several times with a sodium bicarbonate solution and dried over sodium sulfate. The solvent is then removed and the crude product subjected to vacuum distillation. Bpt. 265° at 1.0mm. Calc. for $C_9H_4OS_2Br_2$: C = 30.75; H = 1.05; S = 18.47; Br = 45.34; Analyzed: C = 30.71; H = 1.15; S = 18.23; Br = 45.41.

CHEMICAL 2

Preparation 3-(2,5-dimethylthienyl)-3-(2,5-dibromothienyl)-ketone

To a well stirred mixture of 2,5-dimethyl-3-thenoyl chloride (0.07 mole) and 2,5-dibromothiophene (0.065 mole) in 300 cc anhydrous carbon disulfide, aluminum chloride (0.07 mole) is gradually added. A complex soon forms and HCl evolves. The mixture is well stirred at room temperature for 15 hours and subsequently heated on a steam bath for 3 hours. The complex is broken down with ice/HCl and solvent extracted and this is followed by a similar work up as the above experiment in drying and removing the solvent. The yellow oil is distilled over at 160/0.5 m.m. Calculated for $C_{11}H_8OS_2Br_2$ S = 16.9; Analyzed S = 16.4.

CHEMICAL 3

Preparation of Bis-3-(2,5-dichlorothienyl)-ketone

To a well stirred mixture of 2,5-dichloro-3-thenoyl chloride (0.028 mole) and 2,5-dichlorothiophene (0.025 mole) in dry carbon disulfide (200 c.c.), aluminum chloride (0.025 mole) is gradually added. A deep coloration ensues and the mixture is stirred for 15 hours and subsequently heated on a steam bath for 3 hours. Usual work up and distillation yield a yellow oil, Bpt. 150/1.0 mm. $C_9H_2OS_2Cl_4$ : Calc., C = 32.60; H = 0.62; S = 18.9; Cl = 42.6; Found: C = 33.14; H = 0.87; S = 19.3; Cl = 41.7.

CHEMICAL 4

Preparation of Bis-3-(2,5-dimethylthienyl)-ketone

To a well stirred mixture of 2,5-dimethyl-3-thenoyl chloride (10.0 gr., 0.057 mole) and 2,5-dimethylthiophene (6.3gr., 0.055 mole) in carbon disulfide (300 c.c.), aluminum chloride (7.6 gr., 0.057 mole) is gradually added. HCl evolves and usual procedure gives an oil b.p. 137/0.5 which on standing crystallizes to colorless crystals, mpt. 61° (Y. L. Goldfarb & M. S. Kondakova, Izvest. Adad. Nauk. S.S.S.R., Otdel. Khim. Nauk. 1956, 495–504; CA: 1956: 1674c).

CHEMICAL 5

Preparation of 3-(2,5-dichlorothienyl)-3-(2,5-dibromothienyl)-ketone

To a well stirred mixture of 2,5-dichloro-3-thenoyl chloride (0.05 mole) and 2,5-dibromo thiophene (0.049 mole) in 300 c.c. carbon disulfide, aluminum chloride (0.05 mole) is gradually added. The usual reaction time and conditions followed by the usual work up gives a yellow to orange oil bpt. 160/0.7 mm. Calc. for $C_9H_2OS_2Cl_2Br_2$ Calc. for Cl = 16.8; Found Cl = 17.4.

CHEMICAL 6

Preparation of 2-Thenoyl-3-(2,5-dimethylfuran)

To a well stirred mixture of 2,5-dimethylfuran (9.6 gr., 0.1 mole) and 2-thenoyl chloride (14.6 gr. 0.1 mole) in 250 cc carbon disulfide, aluminum chloride (13.3 gr., 0.1 mole) is gradually added. The usual reaction time, work up and distillation give a yellow oil Bpt. 117-120/0.5 mm. Calc. for $C_{14}H_{10}O_2S$: C = 64.03; H = 4.88; S = 15.54; Found: C = 64.51; H = 5.00; S = 15.36.

CHEMICALS 7 – 29

Using the same procedure as in the foregoing preparations, additional chemicals are made as summarized in Table I, which includes data on the boiling point and structure of chemicals 1 – 6 as well as 7 – 29.

Table II presents analytical data on the chemicals; Table III lists bromine analysis data on certain chemicals.

Table I

Structure and Boiling Point of Chemicals 1 – 29

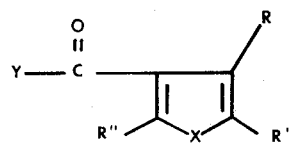

| Chem. | Y | B.pt/mm | X | R | R' | R'' |
|---|---|---|---|---|---|---|
| 7 | $CH_3$—CH=CH— | 80/0.4 | O | H | $CH_3$ | $CH_3$ |
| 8 | $CH_3$—CH=CH— | 95/1.0 | S | H | $CH_3$ | $CH_3$ |
| 9 | o-Bromophenyl | 170/0.5 | S | H | Br | Br |
| 10 | p-Bromophenyl | 170/0.5 | S | H | Br | Br |
| 11 | Phenyl | 115/0.5 | S | H | $CH_3$ | $CH_3$ |
| 12 | p-Chlorophenyl | 137/0.5 | S | H | $CH_3$ | $CH_3$ |
| 13 | p-Chlorophenyl | 160/0.5 | S | H | Br | Br |
| 14 | 2,4-Dichlorophenyl | 135/0.3 | O | H | $CH_3$ | $CH_3$ |
| 15 | 3,4-Dichlorophenyl | 145/0.4 | O | H | $CH_3$ | $CH_3$ |
| 16 | 2,4-Dichlorophenyl | 143/0.3 | S | H | $CH_3$ | $CH_3$ |
| 17 | 3,4-Dichlorophenyl | 155/0.5 | S | H | $CH_3$ | $CH_3$ |
| 18 | 3,4-Dichlorophenyl | 190/0.5 | S | H | Br | Br |
| 19 | 2-Furyl | 140/0.4 | S | H | Cl | Cl |
| 20 | 2-Furyl | 145/0.8 | O | H | $CH_3$ | $CH_3$ |
| 21 | 2-Thienyl | 150/0.3 | S | H | Cl | Cl |
| 22 | 2-Thienyl | 137/0.08 | S | H | $CH_3$ | $CH_3$ |
| 1 | 2-Thienyl | 161/1.0 | S | H | Br | Br |
| 23 | 2-Thienyl | 81/0.5 | S | Br | Br | Br |
| 24 | 3-(2,5-Dibromothienyl) | 162/0.3 | S | H | Br | Br |
| 3 | 3-(2,5-Dichlorothienyl) | 150/1 | S | H | Cl | Cl |
| 4 | 3-(2,5-Dimethylthienyl) | 160/0.5 | S | H | $CH_3$ | $CH_3$ |
| 5 | 3-(2,5-Dichlorothienyl) | 160/0.7 | S | H | Br | Br |
| 2 | 3-(2,5-Dimethylthienyl) | 160/0.5 | S | H | Br | Br |
| 25 | 3-(2,5-Dimethylthienyl) | 155/0.5 | S | H | Cl | Cl |
| 6 | 2-Thienyl | 117/0.5 | O | H | $CH_3$ | $CH_3$ |
| 26 | Phenyl | 132/0.5 | S | $C_2H_5$ | $CH_3$ | $CH_3$ |
| 27 | 2-Thienyl | 155/0.3 | S | $C_2H_5$ | Cl | Cl |
| 28 | 2-Thienyl | 162/1.0 | S | $C_2H_5$ | $CH_3$ | $CH_3$ |
| 29 | 2-(5-Bromothienyl) | 150/0.5 | S | H | Cl | Cl |

Table II

| Chem. | General Formula | Analytical Data (Calc.) | | | | (Found) | | | |
|---|---|---|---|---|---|---|---|---|---|
| | | C | H | S | Cl | C | H | S | Cl |
| 22 | $C_{11}H_{10}OS_2$ | 59.41 | 4.53 | 28.85 | — | 59.46 | 4.50 | 28.54 | — |
| 19 | $C_9H_4O_2SCl_2$ | 44.10 | 1.62 | — | 28.70 | 43.58 | 1.92 | — | 28.74 |
| 20 | $C_{14}H_{10}O_3$ | 69.48 | 5.30 | — | — | 69.84 | 5.80 | — | — |
| 14 | $C_{13}H_{10}O_2Cl_2$ | 57.00 | 3.78 | — | 26.00 | 56.96 | 3.79 | — | 26.30 |
| 15 | $C_{13}H_{10}O_2Cl_2$ | — | — | — | 26.00 | — | — | — | 26.61 |
| 12 | $C_{13}H_{11}OSCl$ | 62.25 | 4.42 | 12.80 | — | 61.56 | 4.44 | 12.87 | — |
| 13 | $C_{11}H_5OSClBr_2$ | 36.00 | 1.58 | 10.04 | — | 37.06 | 1.78 | 9.87 | — |
| 9 | $C_{11}H_5OSBr_3$ | 32.20 | 1.19 | — | — | 33.10 | 1.27 | — | — |
| 10 | $C_{11}H_5OSBr_3$ | 32.20 | 1.19 | — | — | 32.10 | 1.24 | — | — |
| 3 | $C_9H_2OS_2Cl_4$ | 32.60 | 0.62 | 18.9 | 42.6 | 33.14 | 0.87 | 19.3 | 41.7 |
| 5 | $C_9H_2OS_2Cl_2Br_2$ | — | — | — | 16.8 | — | — | — | 17.4 |
| 2 | $C_{11}H_8OS_2Br_2$ | — | — | 16.9 | — | — | — | 16.4 | — |
| 25 | $C_{11}H_8OS_2Cl_2$ | 46.5 | 2.78 | 22.00 | — | 46.6 | 2.99 | 22.01 | — |
| 21 | $C_9H_4OS_2Cl_2$ | 41.0 | 1.54 | 24.4 | 27.0 | 41.2 | 1.61 | 24.1 | 27.1 |
| 16 | $C_{13}H_{10}OSCl_2$ | 54.80 | 3.56 | — | 24.80 | 54.82 | 3.48 | — | 24.47 |
| 17 | $C_{13}H_{10}OSCl_2$ | 54.80 | 3.50 | — | 24.80 | 54.67 | 3.53 | — | 24.18 |
| 1 | $C_9H_4OS_2Br_2$ | 30.71 | 1.15 | 18.23 | — | 30.75 | 1.05 | 18.47 | — |
| 6 | $C_{11}H_{10}O_2S$ | 64.03 | 4.88 | 15.54 | — | 64.51 | 5.00 | 15.36 | — |

Table III

| Chem. | General Formula | Bromine Analysis (Calc.) Bromine | (Found) Bromine |
|---|---|---|---|
| 13 | $C_{11}H_5Br_2OSCl$ | 33.14 | 34.13 |
| 9 | $C_{11}H_5OSBr_3$ | 56.45 | 51.69 |
| 10 | $C_{11}H_5OSBr_3$ | 56.45 | 53.36 |
| 23 | $C_9H_3OS_2Br_3$ | 55.63 | 56.46 |
| 1 | $C_9H_4OS_2Br_2$ | 45.41 | 45.34 |

The following examples will serve to illustrate the practice of the invention in more detail.

EXAMPLE I

This example illustrates the present process for controlling mites.

Cotton, in the primary leaf stage and grown in twelve ounce cups under greenhouse conditions at 70°–75°F, is used in this test. Two plants, for a total of four leaves, are tested at each chemical concentration. The upper leaf surfaces of the untreated leaves are ringed with a one inch diameter circle of tanglefoot, a nontoxic adhesive preparation used on fly papers and for ringing trees. This serves to confine the mites to the upper leaf surface. Mites are transferred to the prepared leaves by placing sections of broad bean leaves heavily infested with two-spotted spider mites, *Tetranychus urticae* L., within the border of the adhesive preparation.

0.2 gram of chemical to be tested may be mixed with one drop of a commercial surface-active dispersing agent such as polyoxyethylated vegetable oil [(e.g. castor oil) as represented for example by such commercial preparations as "Emulphor El" (trademark)], dissolved in 2–4 ml of acetone and brought to a total volume of 100 ml with distilled water. Dilutions of 400 ppm and 80 ppm are made from this solution using distilled water containing one drop of polyoxyethylated vegetable oil per 100 ml distilled water.

The plants are sprayed with dispersions of the chemicals at the various concentrations and the check plants are sprayed with aqueous solutions containing the surface-active agent and acetone without the chemicals.

The sprayings thoroughly wet the upper surface of the leaves. The plants are returned to the greenhouse, allowed to dry, and a count of the mites is made. The plants are held in the greenhouse for five days. A final count of the living mites remaining on the leaves is then made. The percent control is found by using the following formula.

$$\text{Percent Control} = 100 \frac{\left(\begin{array}{c}\text{\% live mites on}\\ \text{check plants}\end{array}\right) - \left(\begin{array}{c}\text{\% live mites on}\\ \text{treated plants}\end{array}\right)}{\text{\% live mites on check plants}}$$

Typical results are shown in Table IV.

Table IV

| Chem. No. | Control of Mites Chemical | % Control at 2000 PPM | % Control at 400 PPM |
|---|---|---|---|
| 9 | 2,5-Dibromo-3-(2-bromobenzoyl) thiophene | 100 | 88 |
| 10 | 2,5-Dibromo-3-(4-bromobenzoyl) thiophene | 100 | 83 |
| 13 | 2,5-Dibromo-3-(p-chlorobenzoyl) thiophene | 100 | 91 |
| 17 | 2,5-Dimethyl-3-(3,4-dichlorobenzoylthiophene) | 100 | 63 |
| 1 | 2-Theonoyl-3-(2,5-dibromothiophene) | 100 | 100 |
| 24 | 2,2',5,5'-Tetrabromo-3,3'-dithienyl ketone | 100 | 100 |
| 3 | 2,2',5,5'-Tetrachloro-3,3'-dithienyl ketone | 100 | 100 |
| 5 | 2,5-Dichloro-2',5'-dibromo-3,3'-dithienyl ketone | 100 | 100 |
| 2 | 2,5-Dimethyl-2',5'-dibromo-3,3' dithienyl ketone | 100 | 100 |
| 25 | 2,5-Dimethyl-2',5'-dichloro-3,3'-dithienyl ketone | 100 | 100 |

EXAMPLE II

This example illustrates the effectiveness of the chemicals as contact poisons for controlling nematodes.

Eighty mg of chemical is mixed with one drop of a commercial surface-active dispersing agent (isoctylphenyl polyethoxy ethanol), dissolved in 2–4 ml acetone, and brought to a total volume of 40 ml with distilled water. This chemical suspension is added to, and manually mixed with, 1.5 pounds of sandy soil severely infested with root-knot nematodes of the genus Meloidigyne. This amount of chemical is equivalent to a rate of 240 pounds per acre. All dosages are based on the weight of an acre of soil 6 inches deep as being two million pounds. Dosages of 120 pounds per acre and sixty pounds per acre are also included. The treated 1.5 pounds of infested soil is filled into two twelve-ounce styrofoam cups and placed in the greenhouse at a temperature of approximately 75°F. Untreated noninfested and infested checks are included in the test.

One week later five cucumber seeds are planted in each treated and untreated cup. The test is kept in the greenhouse and watered regularly. Two weeks after planting the seeds the cucumber roots are inspected for galls caused by the root-knot nematodes. The results are recorded in percent control. Results with the chemicals employed in the present invention are shown in Table V.

TABLE V

| | Control of Nematodes | | | |
|---|---|---|---|---|
| | | Percent Control At | | |
| Chem. No. | Chemical | 240 Lbs/A | 120 Lbs/A | 60 Lbs/A |
| 1 | 2-Thenoyl-3-(2,5-dibromo-thiophene | — | 100 | 100 |
| 21 | 2-Thenoyl-3-(2,5-dichloro thiophene) | 100 | 80 | 60 |
| 13 | 2,5-Dibromo-3-(p-chloro-benzoyl) thiophene | 100 | 40 | 0 |
| 8 | 2,5-Dimethyl-3-crotonoyl thiophene | 90 | 0 | 0 |
| 23 | 2-Thenoyl-3-(2,4,5-Tri-bromothiophene) | 100 | 80 | 40 |
| 24 | 2,2',5,5'-Tetrabromo-3,3'-dithienyl ketone | 80 | 0 | 0 |

EXAMPLE III

This example illustrates the effectiveness of the invention for controlling insects. In this test, fourth instar larvae of *Aedes aegypti* (L.) mosquitoes are used. After hatching, the larvae normally reach this stage of development in five days at 80°F.

One ml of acetone and 100 ml of water is added to 10 ml of each chemical to be tested. This gives a concentration of 100 ppm. A dilution of 10 ppm is made from this solution.

Twenty-five ml portions of each concentration of chemical to be tested, replicated once, are placed in test tubes and from 5 to 25 mosquito larvae are added. Checks without the chemical and plain water checks are also included. The tubes are held in darkness at 70°F for 72 hours. At the end of this period, both live and dead larvae are counted and the percent mortality calculated. The percent mortality of the larvae treated with the present chemicals is shown in Table VI.

TABLE VI

| | Control of Insects | | | |
|---|---|---|---|---|
| | | Percent of Mortality at | | |
| Chem. No. | Chemical | 100 PPM | 10 PPM | 1 PPM |
| 7 | 2,5-Dimethyl-3-crotonoyl furan | 100 | 5 | — |
| 8 | 2,5-Dimethyl-3-crotonoyl thiophene | 100 | 100 | 0 |
| 9 | 2,5-Dibromo-3-(2-bromobenzoyl) thiophene | 100 | 100 | 0 |
| 10 | 2,5-Dibromo-3-(4-bromobenzoyl) thiophene | 100 | 100 | 100 |
| 11 | 2,5-Dimethyl-3-benzoyl thiophene | 100 | 95 | — |
| 12 | 2,5-Dimethyl-3-(p-chlorobenzoyl) thiophene | 100 | 100 | 0 |
| 13 | 2,5-Dibromo-3-(p-chlorobenzoyl) thiophene | 100 | 85 | — |
| 14 | 2,5-Dimethyl-3-(2,4-dichlorobenzoyl) furan | 100 | 0 | — |
| 15 | 2,5-Dimethyl-3-(3,4-dichlorobenzoyl) furan | 100 | 80 | — |
| 16 | 2,5-Dimethyl-3-(2,4-dichlorobenzoyl) furan | 100 | 100 | 25 |
| 17 | 2,5-Dimethyl-3-(3,4-dichlorobenzoyl) thiophene | 100 | 90 | 20 |
| 18 | 2,5-Dibromo-3-(3,4-dichlorobenzoyl) thiophene | 100 | 100 | 100 |
| 19 | 2-Furoyl-3-(2,5-dichlorothiophene) | 100 | 100 | 36 |
| 20 | 2-Furoyl-3-(2,5-dimethylfuran) | 100 | 35 | — |
| 21 | 2-Thenoyl-3-(2,5-dichlorothiophene) | 100 | 100 | 0 |
| 22 | 2-Thenoyl-3-(2,5-dimethylthiophene) | 100 | 100 | 0 |
| 1 | 2-Thenoyl-3-(2,5-dibromothiophene) | 100 | 100 | 50 |
| 23 | 2-Thenoyl-3-(2,4,5-tribromothiophene) | 100 | 100 | 0 |
| 24 | 2,2,5,5'-Tetrabromo-3,3'-dithienyl ketone | 100 | 100 | 20 |
| 3 | 2,2',5,5'-Tetrachloro-3,3'-dithienyl ketone | 100 | 100 | 100 |
| 4 | 2,2',5,5'-Tetramethyl-3,3'-dithienyl ketone | 100 | 100 | 6 |
| 5 | 2,5-Dichloro-2',5'-dibromo-3,3'-dithienyl ketone | 100 | 100 | 100 |
| 2 | 2,5-Dimethyl-2',5' dibromo-3,3'-ketone | 100 | 100 | 0 |
| 25 | 2,5-Dimethyl-2',5'-dichloro-3,3'-dithienyl ketone | 100 | 100 | 0 |
| 6 | 2-Thenoyl-3-(2,5-dimethylfuran) | 100 | 100 | — |

EXAMPLE IV

Table VII gives a selective comparison between (i) certain chemicals employed in the invention (ii) certain chemicals pertinent to U.S. Pat. No. 2,690,413, Janes et al. and (iii) certain chemicals pertinent to British Pat. No. 1,228,744 Boots Pure Drug Co., as follows:

| | Chemical |
|---|---|
| | (i) Chemicals of the present process |
| No. 1 | 2-Thenoyl-3-(2,5-dibromothiophene) |
| No. 24 | 2,2',5,5'-Tetrabromo-3,3'-dithienyl ketone |
| No. 3 | 2,2',5,5'-Tetrachloro-3,3'-dithienyl ketone |
| | (ii) Chemicals pertinent to U.S. 2,690,413 |
| A | 2,5-Dibromo-3-acetylthiophene |
| B | 2,5-Dichloro-3-acetylthiophene |
| | (iii) Chemicals pertinent to British 1,228,744 |
| C | 2,2'-Dithienyl ketone |
| D | 5-Chloro-2-benzothienone |

Table VII shows the results of evaluating the chemicals as acaricides using the procedure previously described.

TABLE VII

| | Activity Comparison on Mites | | |
|---|---|---|---|
| | Percent | Control | at |
| | 2000 PPM | 400 PPM | 80 PPM |
| Chem. 1. | 100 | 100 | 47 |
| Chem. 24 | 100 | 100 | 81 |
| Chem. 3 | 100 | 100 | 72 |
| A | 53 | — | — |
| B | 11 | — | — |
| C | 47 | — | — |
| D | 72 | — | — |

The superiority of the chemicals used in the invention, Chemicals Nos. 1, 24 and 3, is manifest in Table VII.

We claim:

1. A method of controlling acarids, insects or nematodes comprising applying to a locus, subject to attack by acarids, insects or nematodes, an acaricidally, insecticidally or nematocidally effective amount of a substituted furan having the formula

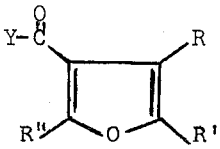

wherein:
Y is selected from the group consisting of alkenyl having from 2 to 8 carbon atoms, furyl, furyl substituted with chlorine, bromine or lower alkyl, thienyl, thienyl substituted with chlorine, bromine or lower alkyl, phenyl, and phenyl substituted with chlorine, bromine or lower alkyl;
R is selected from the group consisting of hydrogen, chlorine, bromine and $C_1$–$C_8$ alkyl;
R' and R'' are the same or different and are selected from the group consisting of chlorine, bromine and $C_1$–$C_8$ alkyl.

2. A method as in claim 1 in which the pests being controlled are acarids, and the said compound is applied in acaricidally effective amount.

3. A method as in claim 2 in which Y has the formula

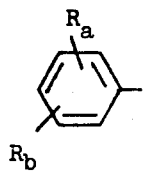

wherein $R_a$ and $R_b$ are the same or different and are selected from the group consisting of hydrogen, chlorine, bromine, and lower alkyl.

4. A method as in claim 2 in which Y has the formula

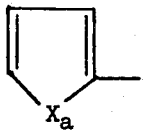

where $X_a$ is selected from the group consisting of oxygen and sulfur.

5. A method as in claim 4 in which $X_a$ is oxygen.
6. A method as in claim 4 in which $X_a$ is sulfur.
7. A method as in claim 2 in which Y has the formula

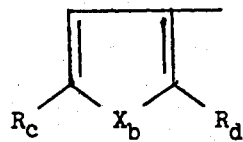

wherein $R_c$ and $R_d$ are the same or different and are selected from the group consisting of hydrogen and lower alkyl, and $X_b$ is selected from the group consisting of oxygen and sulfur.

8. A method as in claim 7 in which $X_b$ is oxygen.
9. A method as in claim 7 in which $X_b$ is sulfur.
10. A method as in claim 2 in which Y is CH —CH=λ CH—, R is hydrogen, and R' and R'' are methyl.
11. A method as in claim 2 in which Y is 2,4-dichlorophenyl, R is hydrogen, and R' and R'' are methyl.
12. A method as in claim 2 in which Y is 3,4-dichlorophyenyl, R is hydrogen, and R' and R'' are methyl.
13. A method as in claim 2 in which Y is 2-furyl, R is hydrogen, and R' and R'' are methyl.
14. A method as in claim 2 in which Y is 2-thienyl, R is hydrogen, and R' and R'' are methyl.

* * * * *